(12) United States Patent (10) Patent No.: US 8,839,470 B2
Ramos et al. (45) Date of Patent: Sep. 23, 2014

(54) MEDICAL IMAGE TABLE ASSEMBLY AND METHOD OF MANUFACTURING THE SAME

(75) Inventors: Ryan Jerome Ramos, Greenfield, WI (US); Nick Patterson, Santa Cruz, CA (US)

(73) Assignee: General Electric Companay, Schenectady, NY (US)

( * ) Notice: Subject to any disclaimer, the term of this patent is extended or adjusted under 35 U.S.C. 154(b) by 84 days.

(21) Appl. No.: 13/250,497

(22) Filed: Sep. 30, 2011

(65) Prior Publication Data

US 2013/0081204 A1 Apr. 4, 2013

(51) Int. Cl.
*A61B 6/04* (2006.01)
*A61B 6/00* (2006.01)
*A61B 6/03* (2006.01)

(52) U.S. Cl.
CPC ............ *A61B 6/0457* (2013.01); *A61B 6/4417* (2013.01); *A61B 6/037* (2013.01); *A61B 6/032* (2013.01)
USPC ............................ 5/601; 5/81.1 R; 5/81.1 HS

(58) Field of Classification Search
USPC .................................. 5/601, 81.1 R, 81.1 HS
See application file for complete search history.

(56) References Cited

U.S. PATENT DOCUMENTS

| | | | |
|---|---|---|---|
| 6,322,251 B1 | 11/2001 | Ballhaus et al. | |
| 6,578,219 B1* | 6/2003 | Gabel et al. | 5/710 |
| 6,640,364 B1 | 11/2003 | Josephson et al. | |
| 7,467,004 B2 | 12/2008 | Calderon et al. | |
| 7,920,910 B2 | 4/2011 | Calderon et al. | |
| 8,621,689 B2* | 1/2014 | Dong et al. | 5/601 |
| 2004/0200001 A1* | 10/2004 | Stolze et al. | 5/601 |
| 2005/0096531 A1* | 5/2005 | Oonuma et al. | 600/409 |
| 2005/0269514 A1* | 12/2005 | Stark | 250/363.08 |
| 2008/0120781 A1* | 5/2008 | Aulbach et al. | 5/601 |
| 2008/0201849 A1* | 8/2008 | Van Es et al. | 5/601 |
| 2008/0209636 A1* | 9/2008 | Riley | 5/601 |
| 2009/0185663 A1* | 7/2009 | Gaines, Jr. | 378/209 |
| 2010/0113913 A1* | 5/2010 | Oosawa | 600/415 |
| 2013/0025054 A1* | 1/2013 | Graw et al. | 5/601 |
| 2013/0074263 A1* | 3/2013 | Driemel et al. | 5/601 |
| 2013/0298328 A1* | 11/2013 | Singh | 5/601 |

* cited by examiner

*Primary Examiner* — William Kelleher
(74) *Attorney, Agent, or Firm* — General Electric Company; Lucas Divine

(57) ABSTRACT

A medical imaging table assembly includes a table portion, a cradle slidably coupled to the table portion, the cradle having a length that defines a patient scanning area and a workflow management area, and a patient support pad disposed only on the patient scanning area. A medical imaging system including the medical imaging table and a method of manufacturing the medical imaging table are also described herein.

19 Claims, 11 Drawing Sheets

MEDICAL IMAGE TABLE ASSEMBLY AND METHOD OF MANUFACTURING THE SAME

BACKGROUND OF THE INVENTION

This subject matter disclosed herein relates generally to imaging systems, and more particularly, to a patient table for a medical imaging system and a method of manufacturing the same.

In at least some imaging system configurations, a patient is positioned on a table that is slidably coupled to a base. When performing medical imaging, such as computed tomography (CT) imaging, the table including the patient, is moved into the bore of the imaging system to perform a scan of the patient. After the scan is completed, the table is operated to remove the patient from the bore of the imaging system. To enable the imaging system to scan patients of various heights, the table typically has a length that is greater than a height of an average patient. Accordingly, only the portion of the table having the patient disposed thereon is inserted into the imaging system during the scan while the remaining portion of the table remains outside the imaging system.

Conventional tables are typically designed to support the patient while the table is fully extended into the imaging system. Accordingly, at least some known tables are fabricated from a substantially rigid material that reduces table sag while the table is extended. To increase patient comfort while the patient is lying on the substantially rigid table, these tables include a pad that is installed on the table and extends over the entire length of the table.

Operators often place devices on the portion of the table that remains outside the imaging system during the scanning procedure. More specifically, operators may place a variety of medically related devices directly on the portion of the pad that is installed on the portion of the table that is not inserted into the imaging system. Placing objects directly on the pad may cause damage to the pad. For example, a liquid spilling on the pad may require that the pad be removed and sterilized prior to subsequent use. Moreover, the pad itself, because of its flexibility, does not provide a substantially stable surface. Accordingly, devices placed directly on the pad may inadvertently fall on the floor resulting in damage to the device.

BRIEF DESCRIPTION OF THE INVENTION

In one embodiment, a medical imaging table assembly is provided. The medical imaging table assembly includes a table portion, a cradle slidably coupled to the table portion, the cradle having a length that defines a patient scanning area and a workflow management area, and a patient support pad disposed only on the patient scanning area.

In another embodiment, a medical imaging system is provided. The medical imaging system includes a gantry having an opening extending therethrough, at least one detector coupled to the gantry, and a table assembly. The table assembly includes a table portion, a cradle slidably coupled to the table portion, the cradle having a length that defines a patient scanning area and a workflow management area, and a patient support pad disposed only on the patient scanning area.

In a further embodiment, a method of manufacturing a medical table assembly comprises providing a table portion, slidably coupling a cradle to the table portion, the cradle having a length that defines a patient scanning area and a workflow management area, and installing a patient support pad only on the patient scanning area.

DETAILED DESCRIPTION OF THE INVENTION

Figure 1:
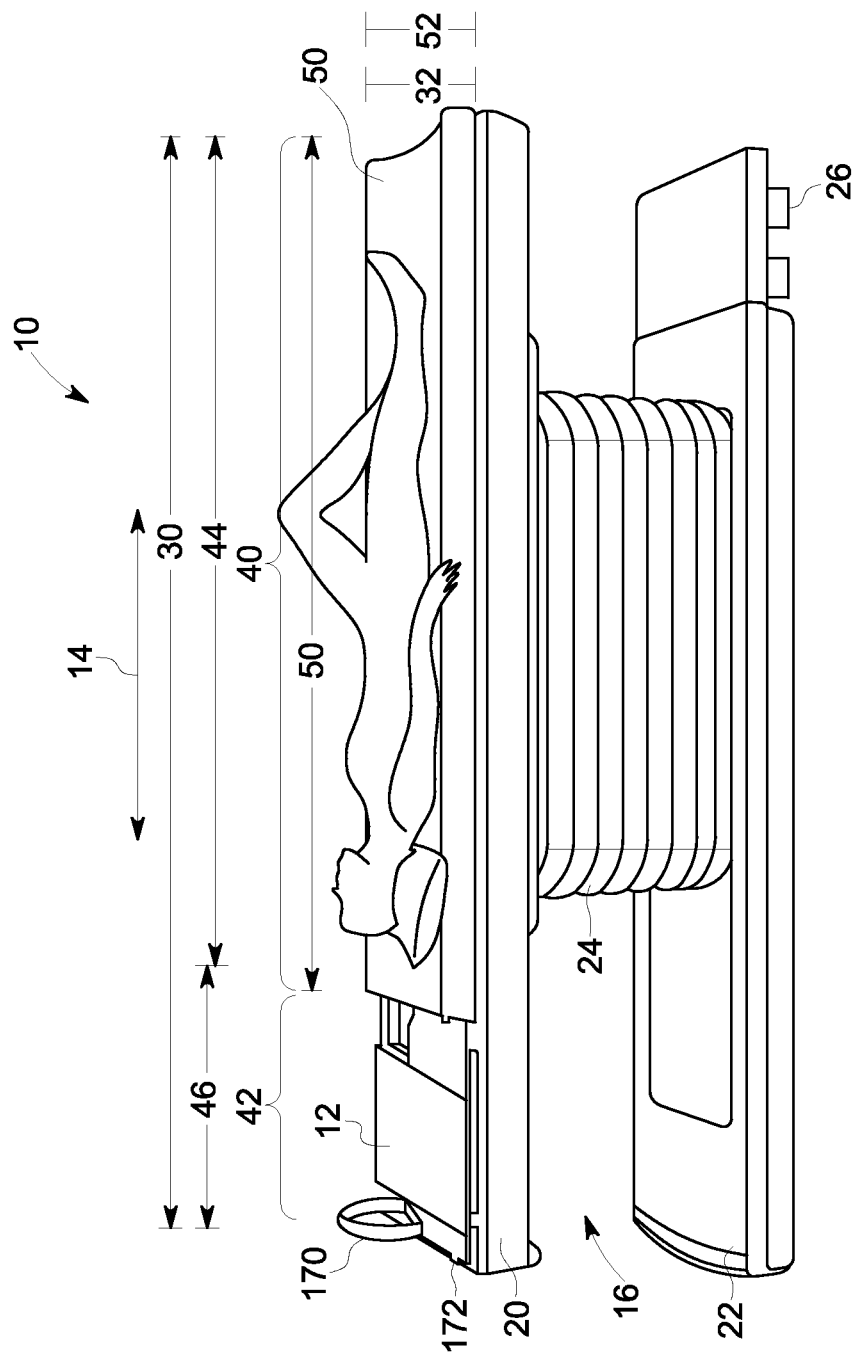
FIG. 1 is a side perspective view of an exemplary medical imaging table assembly formed in accordance with various embodiments.

The foregoing summary, as well as the following detailed description of various embodiments, will be better understood when read in conjunction with the appended drawings. To the extent that the figures illustrate diagrams of the functional blocks of the various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

Described herein in an exemplary medical imaging table assembly that includes a cradle having a portion thereof that defines a workflow management area that is separate from a patient scanning area. The patient scanning area includes a pad to provide patient support during the imaging procedure. The workflow management area provides a stable surface to enable a technician to place various medical equipment. The workflow management area also includes other components, including a tray that is supported by a bridge that suspends the tray above the workflow management area of the cradle.

Figure 2:
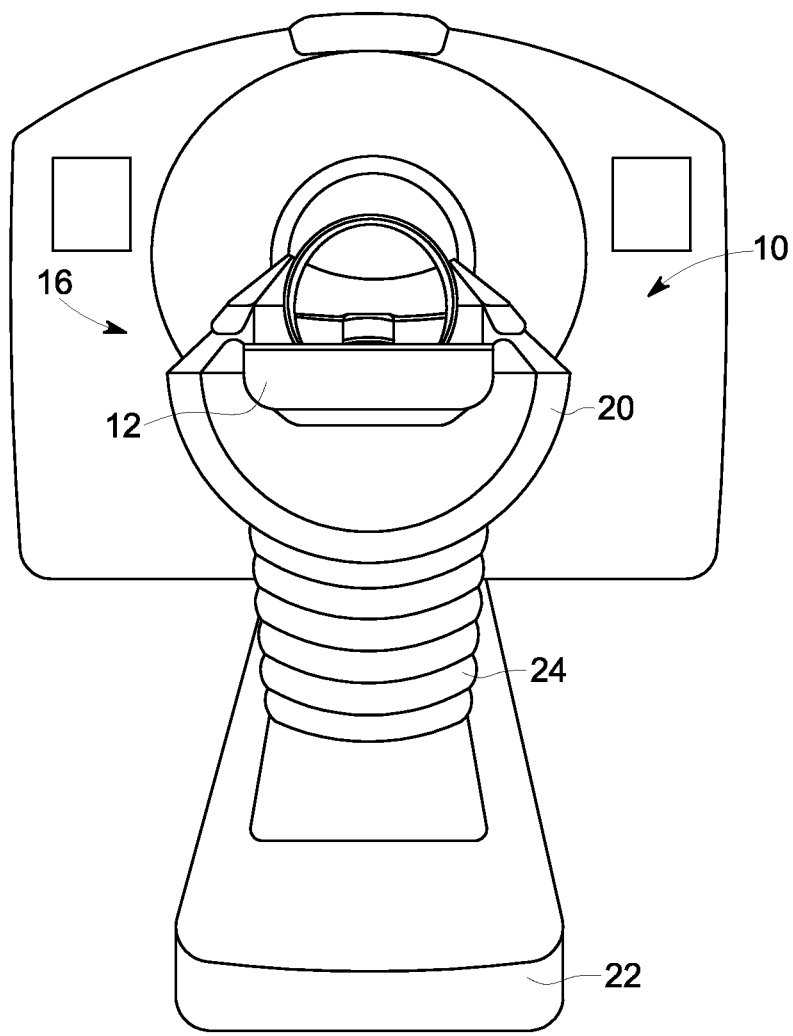
FIG. 2 is a front view of the table assembly shown in FIG. 1 formed in accordance with various embodiments.
Figure 3:
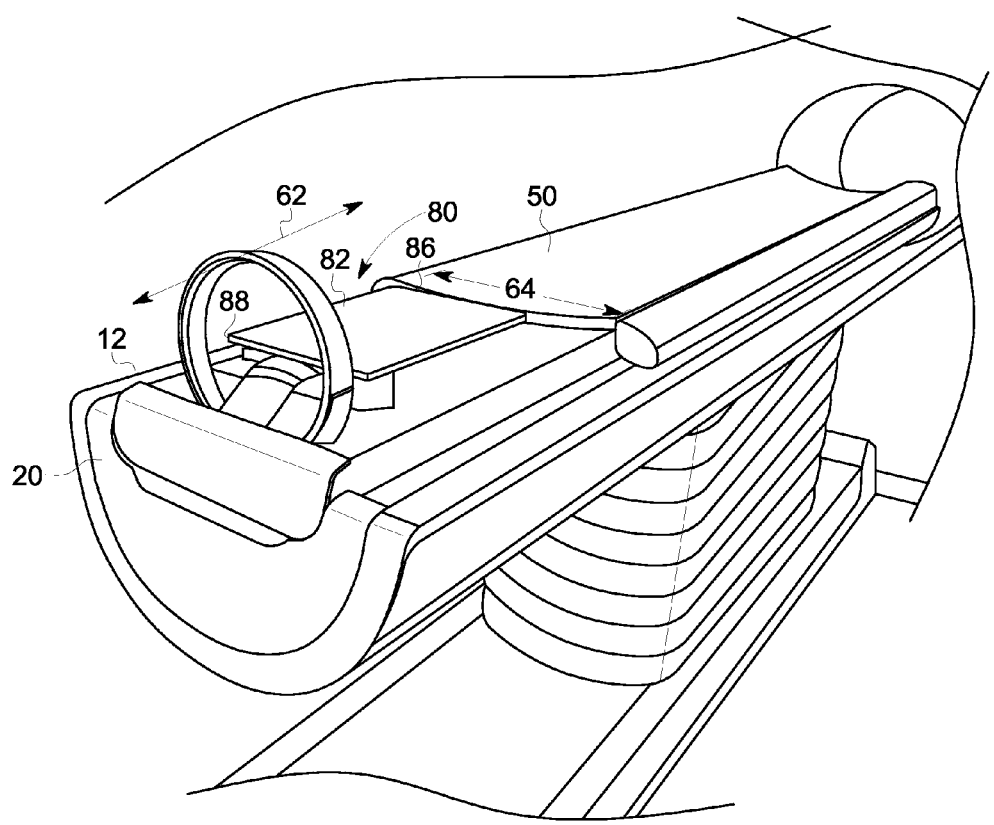
FIG. 3 is a front perspective view of the table assembly shown in FIG. 1 formed in accordance with various embodiments.
Figure 4:
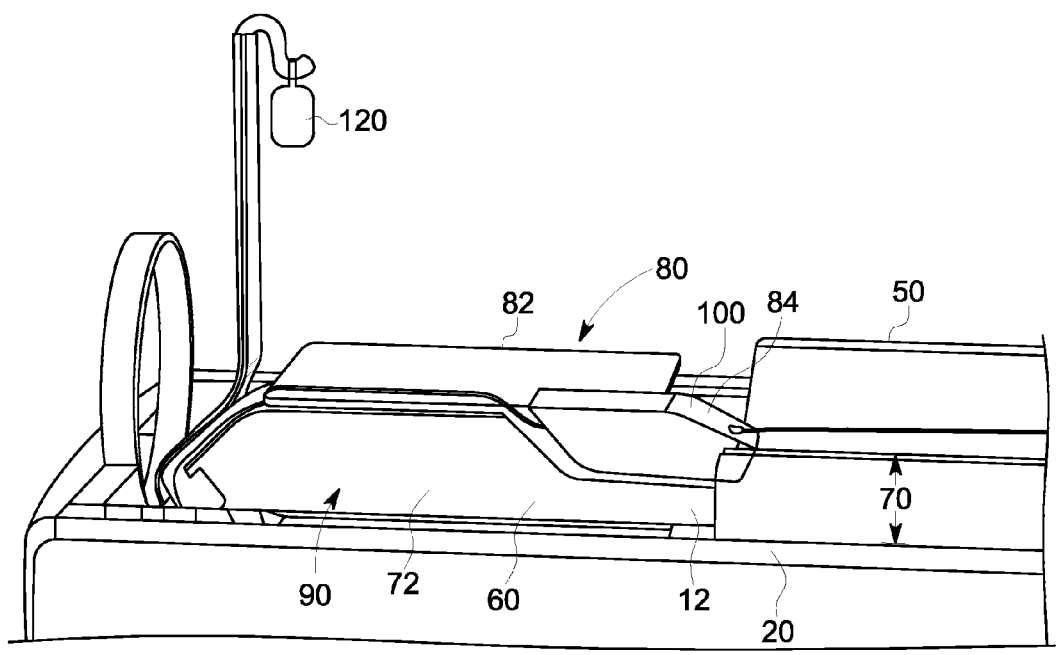
FIG. 4 is a side view of the table assembly shown in FIG. 1 formed in accordance with various embodiments.

FIG. 1 is a side perspective view of an exemplary medical imaging table assembly 10 that is formed in accordance with various embodiments. FIG. 2 is an end view of the medical imaging table assembly 10 shown in FIG. 1. The table assembly 10 may be utilized with various medical imaging systems. For example, the table assembly 10 may be utilized with a Positron Emission Tomography (PET) imaging system, a Single Photon Emission Computed Tomography (SPECT) imaging system, a Computed Tomography (CT) imaging system, a Magnetic Resonance Imaging (MRI) imaging system, an X-Ray imaging system, an ultrasound imaging system, and/or any other imaging systems capable of generating images of a region of interest (ROI). In particular embodiments, the table assembly 10 is utilized with a medical imaging system. The various embodiments are not limited to medical imaging systems for imaging human subjects, but may include veterinary systems as well as non-medical imaging systems. As used herein, the term "patient" may refer to a human patient or any other animal.

The table assembly 10 generally includes a cradle 12 that is adapted to support a patient thereon. The cradle 12 has an elongated support body that extends in a direction along an examination axis 14. In some embodiments, the cradle 12 may be referred to as a couch or a bed. The cradle 12 is movably or slidably engaged to a table portion 16. During operation, a table positioning system (not shown in FIG. 1) may selectively move the patient in the axial direction (e.g., in a direction along the examination axis 14) into and through a central opening formed in an imaging system (not shown in FIG. 1). A table positioning system (not shown in FIG. 1) may be provided to move the cradle 12 along the examination axis 14 to enable the patient to be positioned within a field-of-view (FOV) of an imaging system. The table positioning system is also operable to move the cradle 12 up-down in a vertical manner or side-to-side in a lateral manner. As shown in FIG. 1, the table portion 16 may include a table 20 to support the cradle 12. The table portion 16 may also include a base 22 and a pedestal 24 that is configured to couple the table 20 to the base 22. The base 22 may include a plurality of rollers 26 to enable a technician to position the table assembly 10 with respect to the imaging system.

The cradle 12 has a length 30 and a width 32. The width 32 of the cradle 12 is sufficient to enable the patient to be disposed on the cradle 12. Moreover, the width 32 is smaller than a diameter of the opening in the imaging system to enable the cradle 12 to be at least partially inserted into the imaging system. The length 30 of the cradle 12 is selected to provide both a patient examination area 40 and a workflow management area 42. As used herein, the patient examination area 40 generally includes a portion of the cradle 12 that is utilized to support the patient for imaging. More specifically, the patient is placed on the patient examination area 40 during the imaging procedure. The patient examination area 40 has a length 44 that is pre-selected to accommodate a plurality of different patients of varying heights. Thus, the patient examination area 40 is defined by a portion of the cradle 12. The remaining portion of the cradle 12 forms at least a part of the workflow management area 42 which has a length 46. Thus, the combined length of the patient examination area 40 and the workflow management area 42 is approximately equal to the overall length 30 of the cradle 12.

The table assembly 10 also includes a patient support pad 50 that is mounted on the cradle 12. The patient support pad 50 has a length 52 and a width 54. The width 54 is selected such that the patient support pad 50 is substantially equal to the width 32 of the cradle 12. Optionally, the width 54 of the patient support pad 50 may be selected such that the patient support pad 50 extends over a portion of the sides of the cradle 12 to provide support to the patient being positioned on or being removed from the cradle 12. The length 52 of the patient support pad 50 is selected such that the patient support pad 50 extends over the surface of the patient examination area 40. Thus, the length 52 of the patient support pad 50 is approximately equal to the length 44 of the patient examination area 40. Moreover, the combined lengths of the cradle cover 60 and the patient support pad 50 is approximately equal to the length of the cradle 12. The cradle cover 60 may be fabricated from a planar film such as a carbon fiber film. Optionally, the cradle cover 60 may be fabricated using another suitable material.

In the exemplary embodiment, the patient support pad 50 is fabricated from a deformable material, such as foam, to provide both comfort and support to the patient during the imaging procedure. Accordingly, the patient support pad 50 has a thickness 70 that is preselected to provide both comfort and support. Moreover, the cradle cover 60 has a thickness 72 that is preselected to cover the hardware coupling the cradle 12 to the table 20. In the exemplary embodiment, the thickness 72 of the cradle cover 60 is less than the thickness 70 of the patient support pad to enable the cradle cover 60 to also provide support to any equipment that may be disposed on the cradle cover 60. More specifically, the thickness 72 of the cradle cover is selected to both cover connecting hardware and to also provide a substantially stable surface to stable support for any devices positioned by the operator on the cradle cover 60.

The table assembly 10 also includes at least one tray assembly 80. The tray assembly 80 includes a tray 82 and a bridge 84. The bridge 84 may be fabricated as a metallic frame that is sized not only to provide structural support to the tray 82, but to also extend the tray 82 above the cradle 12 a distance that is sufficient to form a gap 90 thereunder. The tray 82 has a first end 86 and an opposing second end 88. The bridge 84 is configured to couple the tray 82 to the cradle 12 such that a portion of the tray extends over the workflow management area 42. In the exemplary embodiment, the bridge 84 is coupled between the tray first end 86 and the cradle 12 such that the tray second end 88 is cantilevered over the workflow management area 42. Cantilevered as used herein, generally means that only one end of the tray 82 is supported or fixed, via the bridge 84, and the remaining end is not supported or is free standing. However, in some embodiments, additional supports, e.g. legs, may be provided. In the exemplary embodiment, the bridge 84 is coupled to the cradle 12 proximate to the patient support pad 50 and the tray first end 86 is coupled to the bridge 84 such that the gap 90 is formed between the cradle cover 60, or optionally the cradle 12, and the tray 82. In some embodiments, the tray assembly 80 includes a hinge that is coupled between the tray and the bridge 84. In operation, the hinge enables the technician to lift or otherwise maneuver the tray 82 with respect to the bridge 84.

Figure 5:
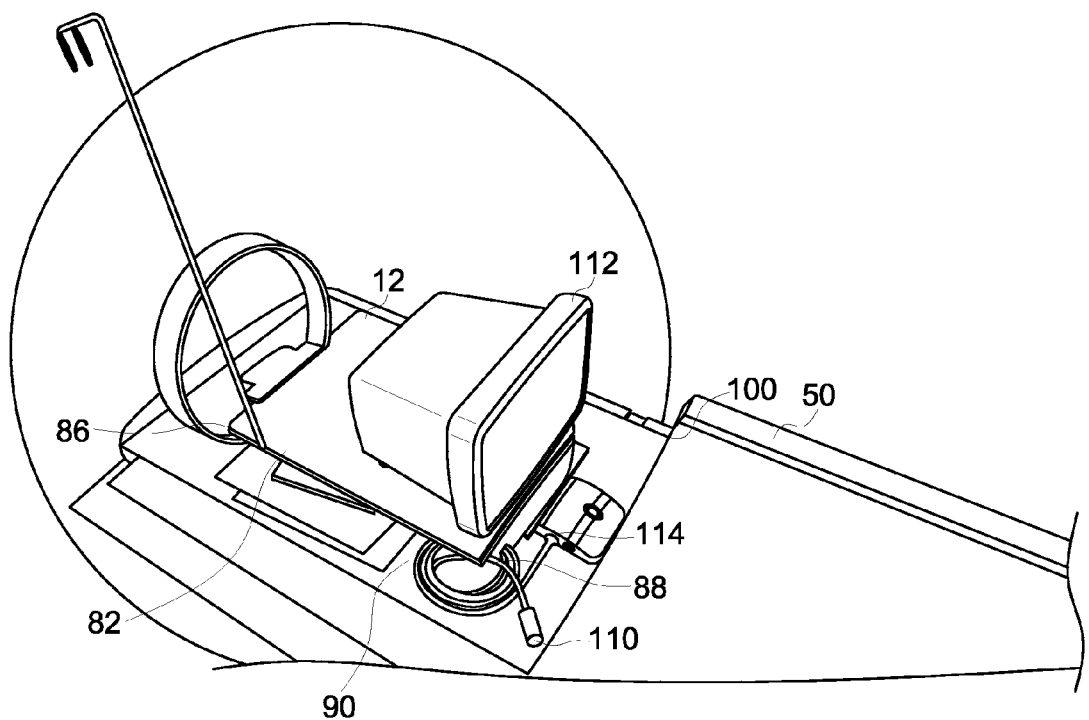
FIG. 5 is a top perspective view of the table assembly shown in FIG. 1 formed in accordance with various embodiments.

FIG. 5 is a top perspective view of a portion of the table assembly 10 shown in FIGS. 1-4. In the exemplary embodiment, the tray 82 is fabricated from a substantially transparent material to enable a technician to visually observe objects located inside the gap 90 and/or under the tray 82. The tray 82 may be fabricated from, for example, a substantially clear plastic material. Optionally, the tray 82 may be fabricated to have a tint that improves the aesthetic appearance of the tray 82 while still enabling an operator to observe objects placed within the gap 90 and/or under the tray 82. Moreover, the tray 82 has a thickness that enables at least one end of the tray 82 to be cantilevered while concurrently providing structural support for any equipment placed on the tray 82. Accordingly, the tray 82 may be fabricated from any substantially transparent material that has a sufficient thickness to provide structural support to objects placed on the tray 82 while concurrently limiting the flexibility of the tray 82. It should be realized that although the table assembly 10 is shown as including a single tray 82, the table assembly 10 may include a plurality of trays 82. More specifically, a second tray (not shown) may be disposed on top of the tray 82 and separated from tray 82 by a gap. Thus, the combination of the cradle 12 and at least one tray 82 forms a multi-level work management area.

Figure 6:
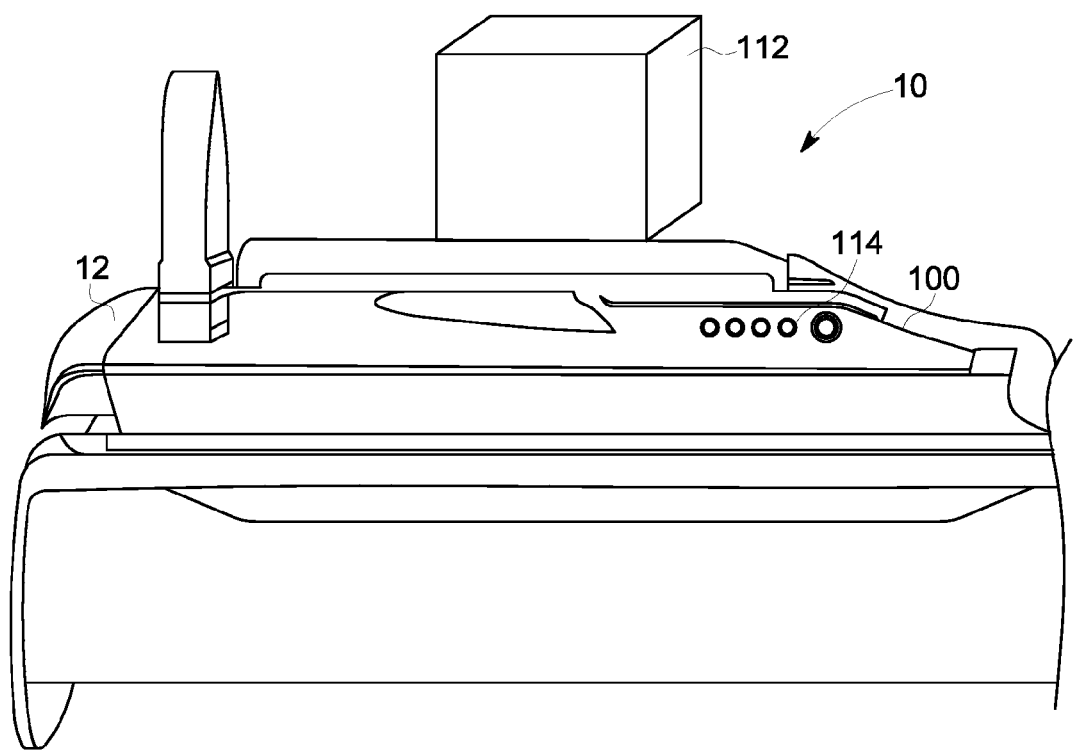
FIG. 6 is another side view of the table assembly shown in FIG. 1 formed in accordance with various embodiments.

FIG. 6 is a side of a portion of the table assembly 10 shown in FIGS. 1-5. As discussed above, in one embodiment, the table assembly 10 includes the bridge 84. The bridge 84 may be fabricated as a metallic frame that is sized not only to provide structural support to the tray 82 but to also extend the tray 82 above the cradle 12 a distance that is sufficient to form the gap 90. In another embodiment, shown in FIGS. 5 and 6, the bridge 84 may be formed as an accessory bridge 100. In operation, the accessory bridge 100 may be configured to support the operation of various medical devices utilized with or separate from the imaging system.

For example, as shown in FIG. 5, the accessory bridge 100 may be utilized to couple a ECG probe 110 to a monitor 112 via the accessory bridge 100. More specifically, the accessory bridge 100 may form a ECG module that includes a plurality of openings 114. At least one of the openings 114 is configured to receive a connector or interface from an ECG probe 110. The output from the monitor 112 is then coupled to another opening in the accessory bridge 100 such that information generated by the ECG probe 110 is transmitted and displayed on the monitor 112. As shown in FIG. 5, in the exemplary embodiment, the monitor 112 may be placed on the tray 82 such that the monitor 112 and the accessory bridge 100 are movable with the cradle 12.

The accessory bridge 100 may also be configured to receive information from other types of sensors and transmit the information to other devices in addition to the monitor 112. For example, the output from an oxygen saturation sensor may be input to the accessory bridge 100 via at least one connector. The output from the oxygen saturation sensor may then be transmitted to the monitor 112 or another medical device to enable the technician to monitor the oxygen level of the patient during the scanning procedure. In operation, the accessory bridge 100 enables the technician to attach various devices to the patient and functions as a movable interconnection between the sensors or devices attached to the patient and other external devices that are used to monitor the sensors.

The accessory bridge 100 may also be configured to receive or transmit a fluid from or to the patient. For example, referring again to FIG. 4, the accessory bridge 100 may be configured to receive a fluid from an intravenous (IV) source 120. The fluid may be supplied to the accessory bridge via a tube 122. The accessory bridge 100 may then transmit the fluid to the patient. Thus, the accessory bridge 100 forms an intermediate connection device that is located between various sensors and other external equipment that enables the quantity of cables to be reduced and also provides a more organized placement for the cables to reduce interference between the cables and the operation of the imaging table assembly 10. Moreover, the accessory bridge 100 may be configured to function as a connection hub to transmit and or receive electrical signals or fluids.

Figure 7:
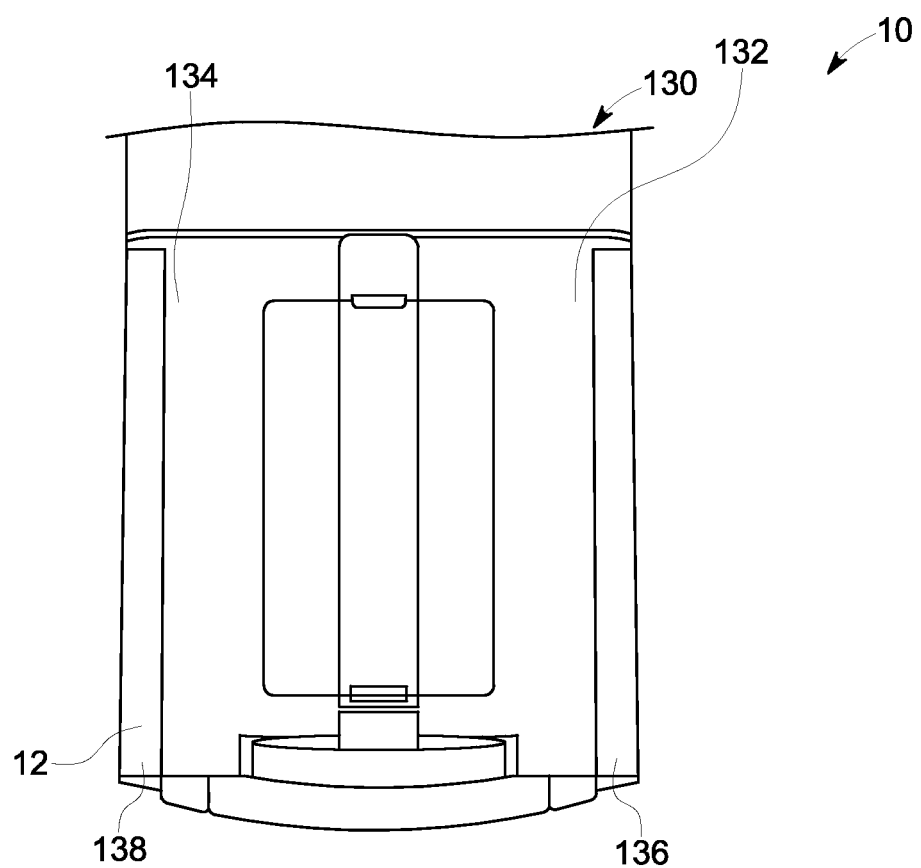
FIG. 7 is a top view of the table assembly shown in FIG. 1 formed in accordance with various embodiments.

FIG. 7 is a top view of the table assembly 10 shown in FIG. 1. In the exemplary embodiment, the table assembly 10 also includes a lighting system 130. The lighting system 130, in one embodiment, includes a first light source 132 and a second light source 134. In the exemplary embodiment, the light source 132 is coupled to a first side 136 of the cradle 12 and the light source 134 is coupled to an opposing second side 138 the cradle 12. Moreover, the lights sources 132 and 134 are disposed between the table 20 and the cradle 12. In operation, the lighting system 130 is configured to illuminate the gap 90 that is defined between the table 20 and the cradle 12. The illumination provided by the lighting system 130 enables a technician to visually observe various objects that are placed on the surface of cradle cover 60 below the tray 82. More specifically, because the tray 82 is fabricated from a substantially transparent material, a technician is able to visually observe various objects placed beneath the tray 82 by looking through the tray 82. Thus, in various embodiments, the operator does not have to bend and peer into the gap 90 to identify various objects placed on the cradle cover 60. Moreover, the lighting system 130 enables the technician operator to identify the connectors on the accessory bridge 100 and therefore enables the technician to more easily couple various devices to the accessory bridge 100.

Figure 8:
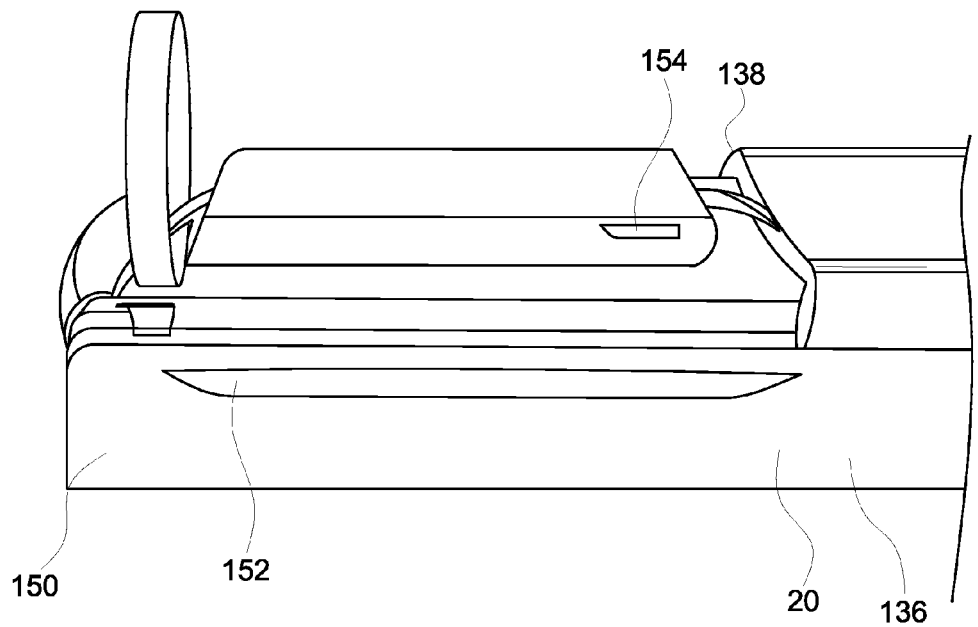
FIG. 8 is another side view of the table assembly shown in FIG. 1 formed in accordance with various embodiments.

FIG. 8 is a side view of the table assembly 10 shown in FIG. 1. In the exemplary embodiment, the table assembly 10 also includes a lighting system 150. In operation, the lighting system 150 identifies the location of the workflow management area 42. The lighting system 150, in some embodiments, includes a first light source 152 and a second light source 154. In the exemplary embodiment, the light source 152 is coupled to the first side 136 of the cradle 12 and the light source 154 is coupled to the opposing second side 138 the cradle 12. Moreover, the lights sources 152 and 154 are disposed beneath the table 20. In operation, the lighting system 150 is configured to illuminate the area between the table 20 and the floor. The illumination provided by the lighting system 150 enables a technician to visually observe the table assembly 10. More specifically, the lighting system 150 may be operable as a "night light" for example that provides a reduced level of illumination to enable an operator to see the edges of the table assembly 10 when the table assembly 10 is disposed is a darkened room, for example. Moreover, the lighting system 150 enables the technician to visually observe various other devices that may be installed beneath the table 20 or positioned on the floor proximate to the table assembly 10.

Referring again to FIG. 1, the table assembly 10 may also include a handle 170. The handle 170 is preferably coupled to an end 172 of the cradle 12. More specifically, the handle 170 is coupled to the end of the cradle 12 that forms the workflow management area 42. In operation, the handle 170 is utilized by the technician to move the cradle 12 into and out of the imaging system. In the exemplary embodiment, the handle 170 has a substantially circular shape to enable the technician to grasp the handle 170 from either side of the cradle 12 or from the end of the cradle 12.

Figure 9:
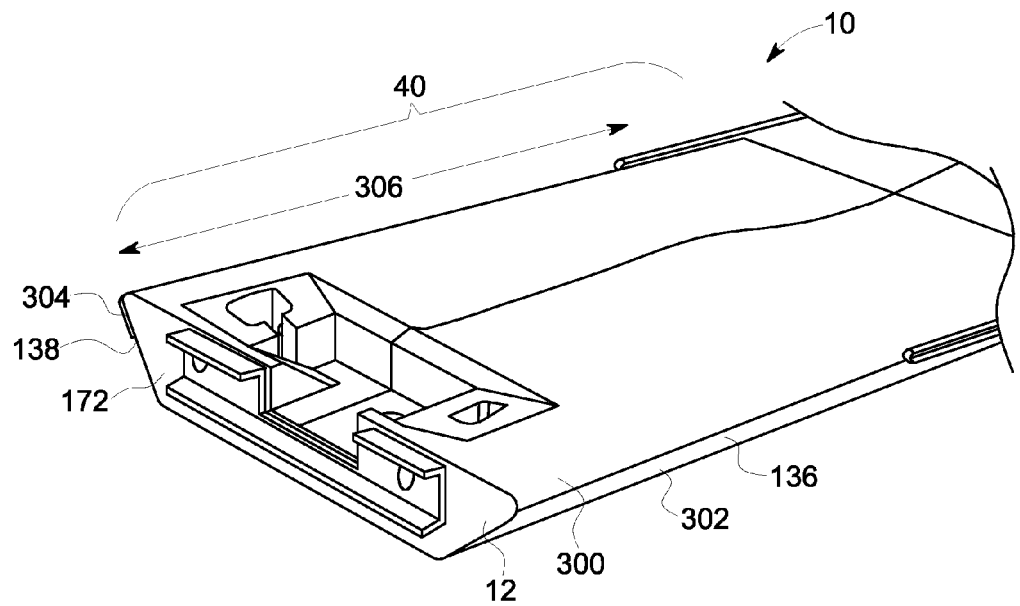
FIG. 9 is a top perspective view of a portion of the table assembly shown in FIGS. 1-8.

FIG. 9 is a top perspective view of a portion of the cradle 12 shown in FIGS. 1-9. In various embodiments, the table assembly 10 may include a secondary cover 300 (shown in FIG. 10). The secondary cover 300 may be used separate from, or in combination with, the cradle cover 60. For example, the secondary cover 300 may be coupled directly to the cradle 12 such that the secondary cover 300 is located between the cradle 12 and the tray 82. Optionally, if the cradle cover 60 is utilized, the secondary cover 300 may be installed on the cradle 12 such that the secondary cover overlays the cradle cover 60 and such that the secondary cover 300 is disposed between the cradle cover 60 and the tray 82. Thus, in various embodiments, the secondary cover 300 forms a part of the workflow management area 40. In operation, the secondary cover 300 provides a cleanable work surface that is removable to be easily cleaned. Moreover, the secondary cover 300 may be cleaned while still attached to the cradle 12. Accordingly, the secondary cover 300 covers various mechanical fasteners and also facilitates preventing fluids from being deposited into hard to reach areas of the cradle 12, thus improving cleanability of the table assembly 10.

In various embodiments, the secondary cover 300 has a shape that is adapted to conform to the cradle 12. For example, the secondary cover 300 includes a first side 302 that is adapted to extend at least partially over the first side 136 of the cradle 12. The secondary cover 300 also includes a second side 302 that is adapted to extend at least partially over the second side 138 of the cradle 12. In the exemplary embodiment, the secondary cover 300 has a length 306 that is substantially the same as the length 46 of the workflow management area 42 to enable the secondary cover 300 to substantially cover the workflow management area 42. The secondary cover 300 may be coupled to the cradle 12 using at least one mechanical fastener. For example, the secondary cover 300 may be coupled to the cradle 12 using hook and loop devices, mechanical fasteners, etc.

Figure 10:
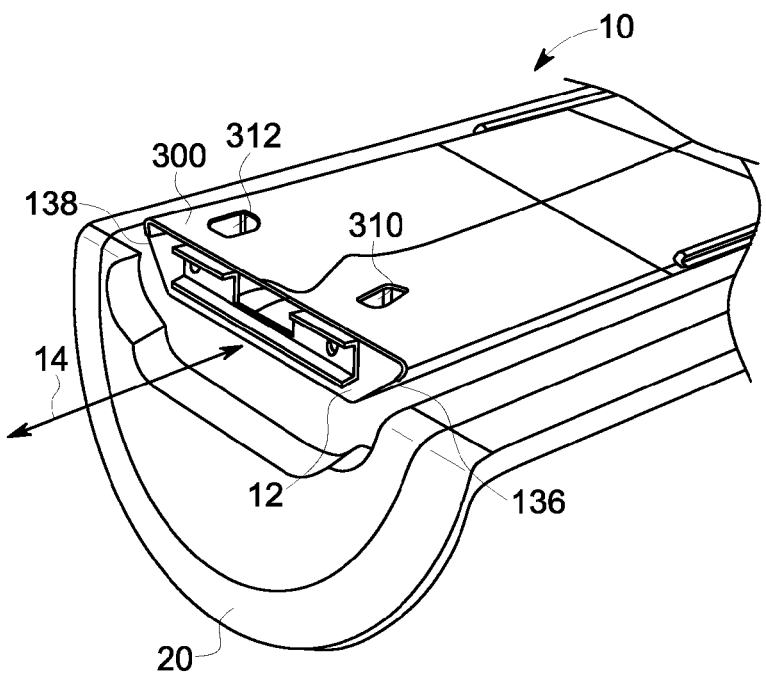
FIG. 10 is a top perspective view of a secondary cover that may be utilized with the table assembly shown in FIGS. 1-8.

FIG. 10 is a top perspective view of the table assembly 10 including the secondary cover 300. In various embodiments, the secondary cover 300 also includes a first opening 310 and a second opening 312. The pair of openings 310 and 312 is configured to be substantially symmetric with respect to the examination axis 14. More specifically, the opening 310 is disposed on one side of the examination axis 14 proximate to the first side 136 and the opening 312 is disposed on an opposite side of the examination axis 14 proximate to the second side 136. The openings 310 and 312 each have a shape that is sized to receive the handle 170 therethrough.

Figure 11:
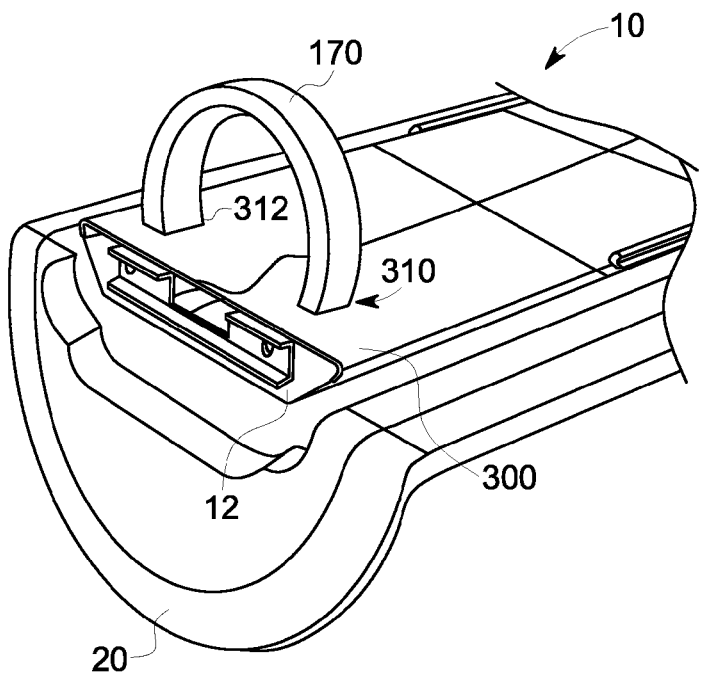
FIG. 11 is another top perspective view of the secondary cover shown in FIG. 10 in accordance with various embodiments.

For example, FIG. 11 is a top perspective view of the table assembly 10 including the secondary cover 300. As shown in FIG. 11, the openings 310 and 312 (shown in FIG. 10) are sized such that the secondary cover 300 forms a seal around the handle 170 to facilitate resisting fluids or other contaminants from passing through the openings 310 and 312 and being deposited on the cradle 12. Accordingly, the openings 310 and 312 are sized to enable each end of the handle to be inserted through a respective opening. Moreover, the openings 310 and 312 are sized such that the secondary cover 300 forms a seal around the handle 170 that is resistant to fluids and/or other contaminants.

Figure 12:
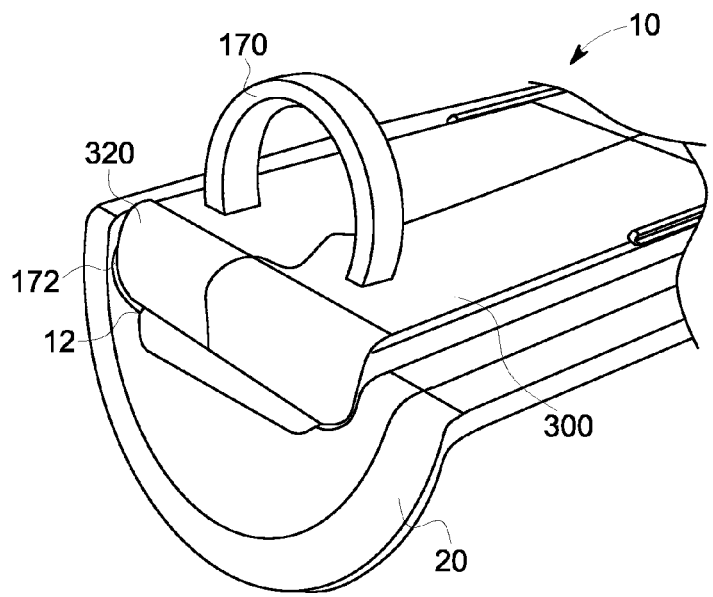
FIG. 12 is another top perspective view of the secondary cover shown in FIG. 10 in accordance with various embodiments.

FIG. 12 is a top perspective view of the table assembly 10 including the secondary cover 300. In various embodiments, the table assembly 10 may also include a cradle end cover 320. The cradle end cover 320 may be formed unitarily with the secondary cover 300 or may be used separately without the secondary cover 300. For example, the cradle end cover 320 may be utilized with the cradle cover 60 when the secondary cover 300 is not installed. In various embodiments, the cradle end cover 320 is coupled to the secondary cover 300 and defines a flap that is adapted to extend over the end 172 of the cradle 12. The cradle end cover 320 may be coupled to the secondary cover 300 using at least one mechanical fastener. For example, the cradle end cover 320 may be coupled to the secondary cover 300 using hook and loop devices, mechanical fasteners, etc. The cradle end cover 320 may also form a padded surface. In operation, the cradle end cover 320 is adapted to provide an aesthetic cover that substantially hides the various mechanical components that are utilized to couple the cradle 12 to the table 20. The cradle end cover 320 is also adapted to reduce any discomfort that may be caused by the operator striking or otherwise contacting the cradle 12 during operation. Moreover, the cradle end cover 320 is adapted to substantially reduce contaminants from entering the area defined between the cradle 12 and the table 20.

Figure 13:
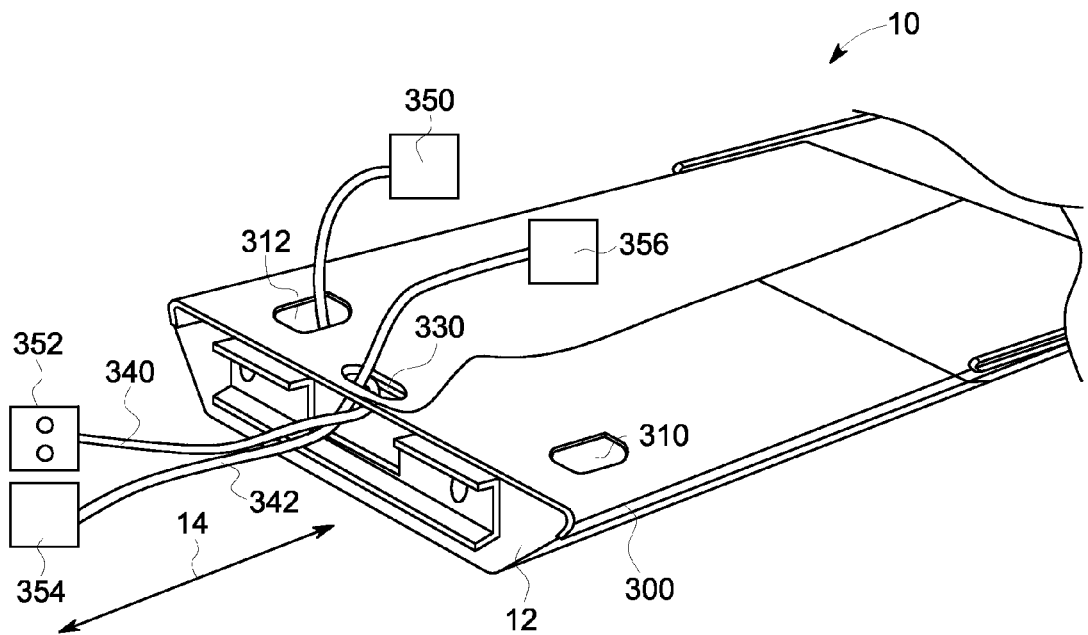
FIG. 13 is a top perspective view of another exemplary cover that may be utilized with the table assembly shown in FIGS. 1-8 in accordance with various embodiments.

FIG. 13 is a top perspective view of the table assembly 10 including another embodiment of the secondary cover 300. In various embodiments, the secondary cover 300 may also include at least one access opening 330. In the exemplary embodiment, the access opening 330 is located along the examination axis 14. The secondary cover 300 may be formed to include both the pair of openings 310 and 312 and the access opening 330. Optionally, the secondary cover 300 may be formed to include either the pair of openings 310 and 312 or the access opening 330. As shown in FIG. 12, when the secondary cover 300 is positioned on the cradle 12 a channel 332 is defined between the secondary cover 300 and the cradle 12. In the exemplary embodiment, the access opening 330 therefore enables various electrical and/or mechanical connections to be routed through the channel 332 and then inserted through the access opening 330 such that the various electrical and/or mechanical connections are accessible by an operator using the workflow management area 42.

For example, in operation, a connection 340 may be routed into the channel 332 and through the opening 330 to enable the operator to connect a device 350 disposed on the cradle 12 and/or the shelf 82, to a power source 352. Moreover, a connection 342 may be routed into the channel 332 and through the opening 330 to enable the operator to connect a device 354, such as a data collection device, to a monitor or other device 356 that is disposed on the cradle 12 and/or the shelf 82. Accordingly, the combination of the opening 330 and the channel 332 enables an operator to electrically and/or mechanically connect any remote device to any other device that is being utilized in the workflow management area 42 of the cradle 12.

By practicing at least one embodiment described herein a table assembly that includes both a patient examination area and a workflow management area is provided. The table assembly includes a patient support pad that extends only over the patient examination area. Because the patient support pad has a length that is less then an overall length of the cradle, the size and thus the cost of the patient support pad may be reduced. Moreover, additional equipment may be placed on the dedicated workflow management area instead of being placed on the patient support pad. Additionally, the accessory bridge provides a movable connection device that enables various sensors to be plugged into the accessory bridge. Moreover, the outputs from the various sensors may be input to various devices placed on the elevated tray coupled to the accessory bridge. The cradle may be fabricated from a carbon fiber material that provides a smooth surface that is easily cleaned and sterilized by the technician in the event fluids are spilled on the cradle. Moreover, the various lighting systems described herein provide increased visual access to the technician while concurrently reducing patient anxiety.

Figure 14:
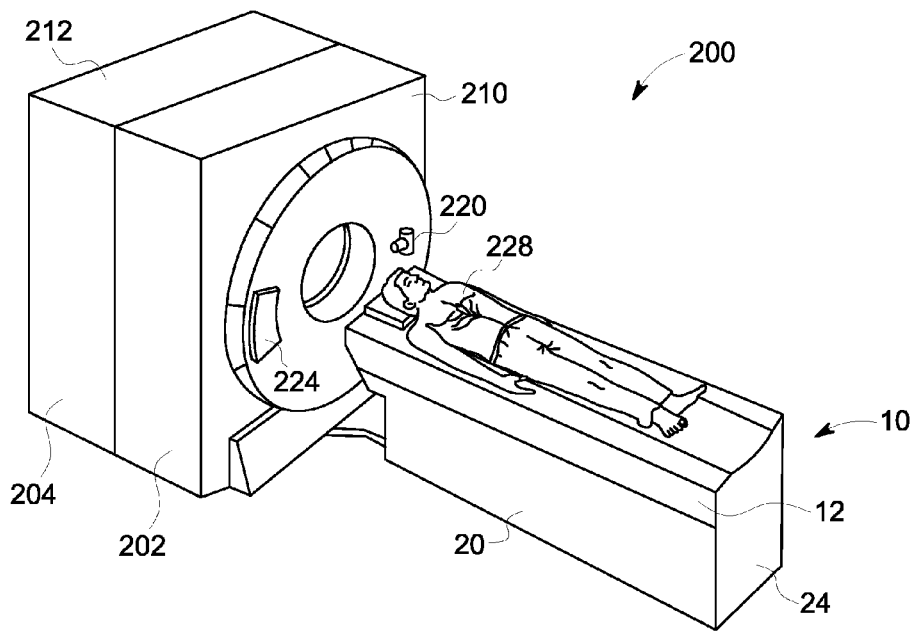
FIG. 14 is a perspective view of an exemplary medical imaging system formed in accordance with various embodiments.
Figure 15:
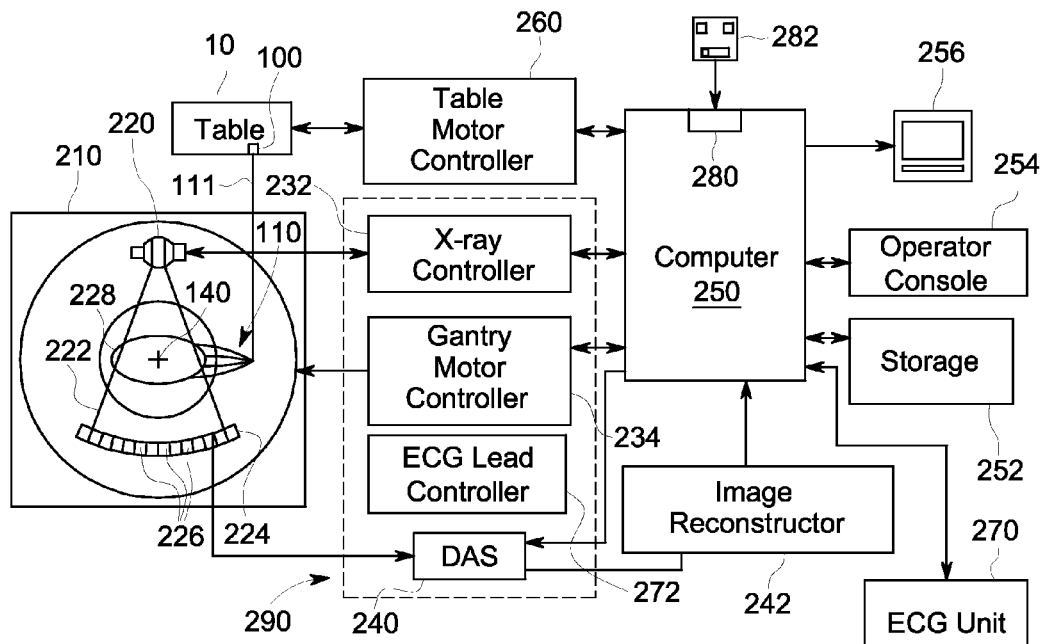
FIG. 15 is a block schematic diagram of one modality unit that forms part of the system illustrated in FIG. 14.

FIG. 14 is a perspective view of an exemplary imaging system 200 that may be utilized with the table assembly 10 described herein. FIG. 15 is a block schematic diagram of one modality unit that forms part of the system illustrated in FIG. 14. In the exemplary embodiment, the imaging system 200 is a multi-modality medical imaging system that includes a first imaging modality unit 202 and a second imaging modality unit 204. The modality units 202 and 204 enable the system 200 to scan an object, for example, a patient, in a first modality using the first modality unit 202 and to scan the object in a second modality using the second modality unit 204. The system 200 allows for multiple scans in different modalities to facilitate an increased diagnostic capability over single modality systems. In one embodiment, the multi-modal imaging system 200 is a Computed Tomography/Positron Emission Tomography (CT/PET) imaging system 200. The CT/PET system 200 includes a first gantry 210 associated with the first modality unit 202 and a second gantry 212 associated with the second modality unit 204. In alternative embodiments, modalities other than CT and PET may be employed with the imaging system 200. The gantry 210 includes an x-ray source 220 that projects a beam of x-rays 222 toward a detector array 224 on the opposite side of the gantry 210. The detector array 224 is formed by a plurality of detector rows (not shown) including a plurality of detector elements 226 that together sense the projected x-rays that pass through an object, such as a patient 228. Each detector element 226 produces an electrical signal that represents the intensity of an impinging x-ray beam and allows estimation of the attenuation of the beam as the beam passes through the object or patient 228.

In the various embodiments, the system 200 also includes the accessory bridge 100 that is formed with the table assembly 10 as discussed above. The accessory bridge 100 receives an input from, for example, an ECG sensor 110 via a at least one lead 111. During a scan to acquire x-ray projection data the gantry 210 and the components mounted thereon rotate about the examination axis 14. The rotation of the gantry 210 and the operation of the x-ray source 220 and the detector 224 are controlled by a control mechanism 230 of the system 200 (e.g., CT/PET system). The control mechanism 230 includes an x-ray controller 232 that provides power and timing signals to the x-ray source 220 and a gantry motor controller 234 that controls the rotational speed and position of the gantry 210 and/or the gantry 212. A data acquisition system (DAS) 240 of the control mechanism 230 samples data from the detector elements 226 and conditions the data for subsequent processing. An image reconstructor 242 receives sampled and digitized x-ray data and emission data from the DAS 240 and performs high-speed image reconstruction. The reconstructed image is transmitted as an input to a computer 250 that stores the image in a storage device 252.

The computer 250 also receives commands and scanning parameters from an operator via console 254 that has an input device, such as, a keyboard. An associated display 256 allows the operator to observe the reconstructed image and other data from the computer 250. Operator supplied commands and parameters are used by the computer 250 to provide control signals and information to the DAS 240, the x-ray controller 232 and the gantry motor controller 234. In addition, the computer 250 operates a table motor controller 260 that controls the motorized table assembly 10 to position the patient 228 in the gantry 210 or 212.

In one embodiment, the computer 250 further receives commands from an ECG unit 270 via a user input, for example, provided as part of the ECG unit 270. The ECG unit 270 controls an ECG lead controller 272 that is communicatively coupled to the patient leads 111. The ECG lead controller 272 and/or the ECG unit 270 may be formed as part of the accessory bridge 100. Accordingly, the ECG lead controller 272 and/or the ECG unit 270 may be formed as part of the table assembly 10. Optionally, the ECG lead controller 272 and/or the ECG unit 270 may be separate from the table assembly 10. The ECG lead controller 272 is configured to control the communication of information between the ECG unit 270 and the patient leads 111.

In one embodiment, the computer 250 includes a read/write device 280, for example, a floppy disk drive, CD-ROM drive, DVD drive, magnetic optical disk (MOD) device, or any other digital device including a network connecting device such as an Ethernet device for reading instructions and/or data from a computer-readable medium 282, such as a floppy disk, a CD-ROM, a DVD or an other digital source such as a network or the Internet, as well as yet to be developed digital means. In another embodiment, the computer 250 executes instructions stored in firmware (not shown). The computer 250 is programmed to perform functions as described herein, and as used herein, the term computer is not limited to integrated circuits referred to in the art as computers, but broadly refers to computers, processors, microcontrollers, microcomputers, programmable logic controllers, application specific integrated circuits, and other programmable circuits, and these terms are used interchangeably herein. The system 200 may also includes a plurality of other detectors, for example, PET detectors (not shown) including a plurality of detector elements. The PET detectors and the detector array 224 both detect radiation and are both referred to herein as radiation detectors.

Additionally, although described in a medical setting, it is contemplated that the embodiments of the invention may be implemented in connection with other imaging systems including industrial CT systems such as, for example, but not limited to, a baggage scanning CT system typically used in a transportation center such as, for example, but not limited to, an airport or a rail station, non-destructive testing systems, etc.

Exemplary embodiments of a multi-modality imaging system are described above in detail. The multi-modality imaging system components illustrated are not limited to the specific embodiments described herein, but rather, components of each multi-modality imaging system may be utilized independently and separately from other components described herein. For example, the multi-modality imaging system components described above may also be used in combination with other imaging systems.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A medical imaging table assembly comprising:
a table portion;
a cradle slidably coupled to the table portion, the cradle having a length that defines a patient scanning area and a workflow management area;
a bridge coupled to the cradle;
a tray having a first end and a second end, the tray first end coupled to the bridge and the tray second end cantilevered over a portion of the workflow management area; and
a patient support pad disposed only on the patient scanning area.

2. The medical imaging table of claim 1, further comprising a cradle cover disposed on the workflow management area, the cradle cover having a thickness that is less than a thickness of the patient support pad.

3. The medical imaging table of claim 1, further comprising a hinge coupling the tray to the bridge.

4. The medical imaging table of claim 1, wherein the tray is fabricated from a transparent material.

5. The medical imaging table of claim 1, further comprising:
a tray lighting system configured to illuminate an area between the tray and the workflow management area.

6. The medical imaging table of claim 1 further comprising a table lighting system configured to illuminate an area between the table and a floor and identify the workflow management area.

7. The medical imaging table of claim 1, wherein the bridge acts as a connection hub to transmit and receive electrical signals or fluids.

8. The medical imaging table of claim 1, further comprising at least one leg situated between the tray and the cradle, providing support to the tray.

9. A medical imaging table assembly comprising:
a table portion;
a cradle slidably coupled to the table portion, the cradle having a length that defines a patient scanning area and a workflow management area;
a patient support pad disposed only on the patient scanning area; and
an electrocardiogram (ECG) bridge coupled to the cradle, the ECG bridge comprising at least one receptacle configured to receive at least one ECG connector.

10. The medical imaging table of claim 9, further comprising:
an ECG module coupled to the ECG bridge; and
a tray having a first end and a second end, the tray first end coupled to the ECG module and the tray second end cantilevered over a portion of the workflow management area.

11. A medical imaging system comprising:
a gantry having an opening extending therethrough;
at least one detector coupled to the gantry; and
a table assembly comprising:
a table portion mounted external to the gantry;
a cradle slidably coupled to the table portion, the cradle configured to be at least partially inserted into the gantry opening, the cradle having a length that defines a patient scanning area and a workflow management area;
a bridge coupled to the cradle;
a tray having a first end and a second end, the tray first end coupled to the bridge and the tray second end cantilevered over a portion of the workflow management area; and
a patient support pad disposed only on the patient scanning area.

12. The medical imaging system of claim 11, wherein the table assembly further comprises a cradle cover disposed on the workflow management area, the cradle cover having a thickness that is less than a thickness of the patient support pad.

13. The medical imaging system of claim 11, wherein the table assembly further comprises:
an electrocardiogram (ECG) module coupled to the cradle.

14. The medical imaging system of claim 11, wherein the bridge is an electrocardiogram (ECG) bridge comprising a junction box configured to receive at least one ECG lead.

15. The medical imaging system of claim 11, wherein the tray is fabricated from a transparent material.

16. The medical imaging system of claim 11, wherein the table assembly further comprises:
a tray lighting system configured to illuminate an area between the tray and the workflow management area.

17. A method of manufacturing a patient table assembly, said method comprising:
providing a table portion;
slidably coupling a cradle to the table portion, the cradle having a length that defines a patient scanning area and a workflow management area;
installing a patient support pad only on the patient scanning area;
coupling a bridge to the cradle; and
coupling a tray to the bridge, a portion of the tray being cantilevered over a portion of the workflow management area.

18. A method of manufacturing a patient table assembly, said method comprising:
providing a table portion;
slidably coupling a cradle to the table portion, the cradle having a length that defines a patient scanning area and a workflow management area;

installing a patient support pad only on the patient scanning area;

coupling an electrocardiogram (ECG) module to the cradle; and coupling a tray to the ECG module to enable a portion of the tray to cantilever over a portion of the workflow management area.

19. A medical imaging table assembly comprising:

a table portion;

a cradle slidably coupled to the table portion, the cradle having a length that defines a patient scanning area and a workflow management area;

a patient support pad disposed only on the patient scanning area;

an electrocardiogram (ECG) module coupled to the cradle; and a tray having a first end and a second end, the tray first end coupled to the ECG module and the tray second end cantilevered over a portion of the workflow management area.

* * * * *